United States Patent [19]
Fago et al.

[11] Patent Number: 5,883,615
[45] Date of Patent: Mar. 16, 1999

[54] FOOT-OPERATED CONTROL SYSTEM FOR A MULTI-FUNCTION

[75] Inventors: Frank M. Fago, Mason; Bill Pollack, Cincinnati; Brian J. Poland, Fairfield, all of Ohio

[73] Assignee: Liebel-Flarsheim Company, Cincinnati, Ohio

[21] Appl. No.: 536,272

[22] Filed: Sep. 29, 1995

[51] Int. Cl.$^6$ .................................................... G09G 5/00
[52] U.S. Cl. ...................... 345/156; 307/119; 200/86.5
[58] Field of Search .................................. 345/156, 157; 307/119; 200/86.5; 606/34

[56] References Cited

U.S. PATENT DOCUMENTS

| | | |
|---|---|---|
| 804,595 | 11/1905 | Garhart . |
| 1,919,968 | 7/1933 | Trabold . |
| 2,040,672 | 5/1936 | Richter . |
| 2,199,963 | 7/1940 | Romberger . |
| 2,293,409 | 8/1942 | Smith . |
| 2,384,805 | 9/1945 | Arens . |
| 2,460,494 | 2/1949 | Eisenberg et al. . |
| 2,482,540 | 9/1949 | Furnas et al. . |
| 2,707,036 | 4/1955 | Hollub . |
| 2,762,891 | 9/1956 | Hill et al. . |
| 3,381,565 | 5/1968 | Haile . |
| 3,399,287 | 8/1968 | Euler . |
| 3,536,229 | 10/1970 | Boros . |
| 3,598,947 | 8/1971 | Osborn . |
| 3,663,772 | 5/1972 | Grabel et al. . |
| 3,833,782 | 9/1974 | Bartel . |
| 3,841,172 | 10/1974 | Pilch . |
| 3,916,719 | 11/1975 | Zwerenz . |
| 3,963,890 | 6/1976 | Straihammer . |
| 3,980,848 | 9/1976 | Schulz et al. . |
| 3,980,849 | 9/1976 | Straihammer . |
| 3,983,344 | 9/1976 | Straihammer ........................ 200/86.5 |
| 4,064,769 | 12/1977 | Amdall et al. .......................... 477/115 |
| 4,354,838 | 10/1982 | Hoyer et al. ............................ 433/101 |
| 4,417,875 | 11/1983 | Matsui ..................................... 433/101 |
| 4,527,983 | 7/1985 | Booth ......................................... 440/7 |
| 4,543,569 | 9/1985 | Karlstrom ............................... 340/539 |
| 4,558,194 | 12/1985 | Wiblin ................................. 200/61.89 |
| 4,586,398 | 5/1986 | Yindra ...................................... 74/512 |
| 4,779,481 | 10/1988 | Natzke et al. ............................ 74/512 |
| 4,983,901 | 1/1991 | Lehmer .................................. 318/685 |
| 5,091,656 | 2/1992 | Gahn ...................................... 307/119 |
| 5,268,624 | 12/1993 | Zanger .................................. 318/551 |
| 5,300,296 | 4/1994 | Stoeckl .................................. 424/427 |
| 5,340,953 | 8/1994 | Krebs et al. ........................... 200/86.5 |
| 5,422,521 | 6/1995 | Neer et al. ............................. 307/119 |
| 5,455,766 | 10/1995 | Scheller et al. ............................ 606/4 |
| 5,626,575 | 5/1997 | Crenner .................................... 606/34 |

*Primary Examiner*—Richard A. Hjerpe
*Assistant Examiner*—Francis Nguyen
*Attorney, Agent, or Firm*—Wood, Herron & Evans, LLP

[57] ABSTRACT

A foot-operated control device system coupleable to a multi-function apparatus comprises a body for positioning on a floor surface and a mode switch manipulatable by the foot of an operator to switch the control device between a dedicated operational mode and an icon operational mode. An actuator is engageable by the operator's foot, and the system operates to actuate a dedicated function of the multi-function apparatus with the system in the dedicated operational mode. Another actuator operates to actuate another dedicated function when the system is in the dedicated operational mode. The one actuator is further operable to select a function of the apparatus when the system is in the icon mode and the other actuator is further operable to actuate the selected function whereby the multi-function apparatus may be selectively operated in the dedicated operational mode for some functions of the apparatus and in the icon operational mode for other functions at the discretion of the operator.

20 Claims, 4 Drawing Sheets

FOOT-OPERATED CONTROL SYSTEM FOR A MULTI-FUNCTION

FIELD OF THE INVENTION

This invention relates to foot-operated control systems for apparatus having multiple selectable functions.

BACKGROUND OF THE INVENTION

Many machines and devices today are configured to perform a variety of different selectable functions or processes. Such multi-function devices are usually equipped with some kind of control mechanism to allow an operator to select and actuate a particular function from the numerous available functions which the device is capable of performing. For example, one such multi-function device used today is a medical operating/imaging table having a patient bearing surface to hold a patient during an operation. The patient bearing surface may be moved laterally and vertically, as well as rotated, in relation to an operating physician to place the patient in a position more convenient for access and operation by the physician. Such operating/imaging tables are equipped with x-ray, tomographic, and fluoroscopic imaging hardware systems which may be used to perform various imaging techniques on the patient to generate real-time or photographic still images to be viewed by the physician. Such tables are operated by multi-function control systems. An example of such a table is the HUT IV urology table available from Liebel-Flarsheim of Cincinnati, Ohio.

One type of control mechanism for a combination operating/imaging table is a hand held unit with a plurality of buttons which are depressed to execute the various functions of the imaging hardware as well as to move the table surface in a desired direction. However, a hand-held control unit requires the physician to interrupt the ongoing medical operation to perform the task of moving the table or making a picture image of the patient. In the least, a hand-held control unit requires that one hand of the physician is free from the medical operation in order to manipulate the control unit. As may be appreciated, it is undesirable, and often impossible, for the physician to have one hand free to manipulate the hand control. Such circumstances usually arises when the surgical procedure is very precise and sensitive and interruption of the procedure is not an alternative.

In some situations it may be possible to utilize assisting medical personnel to operate the hand control unit in order to move the table and operate the imaging hardware. However, such a procedure requires additional trained personnel, increasing the cost of the operation and drawing those personnel from other more critical tasks at hand, such as assisting the operating physician with the medical operation. Additionally, the hands of the operating physician and assisting personnel are usually sterilized, and maintaining the sterility of their hands while they operate the control unit adds another difficulty to the operation scenario. Still further, it is often easier and more efficient for the physician performing the operation to be able to operate the table himself without constantly giving verbal commands for its operation to someone else.

One solution that has been offered as an alternative to a hand control unit is a foot-operated control system having a variety of engageable devices such as buttons, pedals or joysticks which may be manipulated by an operator's feet to leave the operator's hands free to perform other tasks, such as during a medical operation. While foot-operated control systems have been suitable for a variety of different multi-function apparatuses, such control systems have generally been limited in the number of discrete and dedicated functions which they can control. Various considerations must be taken into account when utilizing a foot-operated system including the size of the system and its mobility as well as the positioning of the manipulatable actuation devices within the system.

For example, the dexterity of an operator with respect to their feet is much more limited than their hand dexterity, especially when the operator is wearing shoes as will normally be the case. Therefore the actuation devices of the system must be appropriately sized and spaced for suitable actuation by a foot without the inadvertent actuation of other actuation devices of the system. Consequently, the number of discrete and dedicated functions which may be handled by a foot-operated control system is spatially limited because otherwise the system would be too difficult to use. An operator would constantly be engaging the wrong actuator if such actuators are spaced too closely or are too small.

Increasing the overall size of the foot-operated control system is also not a suitable alternative. The added size and weight reduces mobility which is important because the control system often has to be positioned around the device, such as around the table top of a urology table. Furthermore, a control system which is increased in size to handle an increasing number of dedicated functions, may utilize actuation devices which are spaced so far apart from each other that foot actuation becomes difficult, requiring the operator to shift around unnecessarily during operation of the multi-function apparatus.

Despite the physical limitations of foot-operated control systems, there are an ever-increasing number of functions or multi-function apparatuses which must be accessed and controlled by an operator, such as, x-ray, tomography, fluoroscopy functions for use with an operating table. Therefore, there is a need for a foot-operated control system which can handle a large of different functions without unnecessarily increasing the size of the system or complicating its operation by using small, closely-spaced actuators.

Furthermore, as may be appreciated, an operator of a multi-function apparatus, such as a physician moving a patient and the imaging hardware of an operating/imaging table, should stay focused upon the task at hand, e.g., the surgical operation. A control system with a large number of small, spaced-apart actuation devices which are difficult to engage requires the physician to constantly think about which of the multiple dedicated functions he is selecting or to continually look down at the floor to determine whether he is moving the proper actuation device. The distractions undesirably take the physician's concentration from his primary operation task. The secondary task of controlling the multi-function apparatus should not override the primary task of the operator.

One proposed solution to large and complicated foot-control systems is disclosed in U.S. Pat. No. 5,422,521 entitled FOOT OPERATED CONTROL SYSTEM FOR A MULTI-FUNCTION DEVICE which is commonly owned with the invention of the present application. The foot-operated control system disclosed in U.S. Pat. No. 5,422,531 utilizes a movable foot pedal which is operably coupled to a menu which includes a plurality of selectable functions. When the foot pedal is pivoted to the right or left, a visual indicator moves along the menu and when the pedal is returned to a center position, the visual indicator stops at a selected icon which coincides with a selected function.

Pivoting the pedal downwardly then actuates the selected function. The system may be expanded to accommodate a large number of selectable functions without substantially affecting the complexity of the foot pedal device. Pivoting of the foot pedal moves the indicator through the menu; therefore, a very large number of selectable functions might be utilized limited only by the electronic or mechanical devices necessary to execute the selected functions.

While such a system has proven to be easy to use and readily expandable to handle a large number of functions, Applicants have discovered that some operators are uncomfortable with constantly referring to the menu for activating a function, particularly, for various frequently-used functions. For example, a physician will often move the table top of a urology table to move a patient forward, backward, side-to-side, or rotationally to more easily perform a surgical operation or to make photographic images of a desired region of a patient's body. Such table top and patient movement is frequently done during an operation and particularly when the physician is concentrating on the operation. Requiring the physician to look away to a menu, interrupts the operation. Additionally, some physicians develop an instinctive feel for the foot-operated control system when executing frequently-used functions and constant referral to the menu removes the easy, rapid instinctual control. Therefore, it is desirable to execute certain frequently-used dedicated functions of a multi-function apparatus without requiring the operator to divert his focus to the task at hand, such as to view a menu.

Accordingly, it is an object of the present invention to provide a foot-operated control system which addresses the needs of a large number of operators for control of diverse multi-function apparatuses.

Particularly, it is an objective of the invention to increase the comfort and ease of controlling a multi-function apparatus by foot manipulation.

It is a further objective of the present invention to control a large number of functions of a multi-function apparatus while allowing an operator to maintain focus on a particular more important task while executing certain frequently-used functions.

It is a further objective of the present invention to provide a foot-operated control system which may be readily and easily used to execute certain functions while simultaneously being expandable to execute other functions of an apparatus.

It is still a further objective of the invention to provide instinctual control of frequently-used functions of a multi-function apparatus such as a urological table.

These and other objectives will be more clearly illustrated below by the summary and detailed description of the invention.

SUMMARY OF THE INVENTION

The foot-operated control system of the present invention is operable to be coupled to a multi-function apparatus to actuate one of a number of selectable functions of the apparatus. The control device comprises a body which is configured to be positioned on a floor surface proximate the apparatus. A plurality of actuators are supported by the body for foot engagement to select and execute a desired function. The control device may be switched between a dedicated operational mode and an icon operational mode. In the dedicated operational mode, the actuators are dedicated to certain frequently-used functions, while in the icon operational mode, the actuators are engaged to select functions along an icon display which operates as a function menu. The actuators are then subsequently engaged to execute the selected function of the apparatus. The selectable dedicated and icon modes of the foot-operated control system of the invention provide a system which is readily and easily utilized by an operator for instinctual execution of certain functions without diverting attention away from the primary operation. The inventive-system further provides for expandability in the system to incorporate other functions without unnecessarily complicating the foot operation of the control system or increasing the size of the system.

In a preferred embodiment of the invention, the control system is constructed for a urology table which incorporates a moveable table top and a variety of x-ray, tomography and fluoroscopy functions. Four actuator foot pedals are arranged linearly across the front of the system body which is configured to rest on the floor below the table top. When the control system is in the dedicated operational mode, each actuator pedal is dedicated to a particular frequently-used function. Preferably, the actuator pedals are utilized to raise the table, lower the table, and tilt the table into two directions.

The system further comprises a cross-shaped joystick actuator wherein engagement of a particular leg of the cross by an operator's foot will move the table top forward, backward or to either side. The cross-shaped joystick actuator is angled with respect to the floor surface for easy manipulation by the foot. The rearwardmost and side legs of the cross are wedge shaped such that their engageable surfaces are elevated for easier operation. Particularly, the rearwardmost leg of the cross-shaped joystick is wedge shaped to have a surface elevated higher than the forwardmost and side leg surfaces while the side legs have surfaces elevated higher than the rearwardmost leg surface. This provides more easy access to the legs furthest from the front without inadvertent manipulation of one of the other cross legs.

When the system is in the icon operational mode, two of the actuator pedals provide selection of a function from the icon display while another of the actuator pedals provides execution of the selected function. In a preferred embodiment of the invention, the four pedals are divided with two pedals on the right side of the body and two pedals on the left side of the body. When one of the right-side actuator pedals is engaged by the operator's foot, the control device is responsive to move a visual indicator through the various segments of the icon display to select a function. One pedal moves the indicator in one direction while the other pedal moves the indicator in the opposition direction through the icon display. The left side pedals are utilized to actuate the selected function. That is, when either of the left-side pedals are engaged by an operator's foot with the control system in the icon operational mode, the control system is responsive to execute the selected function of the multi-function apparatus. Therefore, an operator may utilize the present system in the dedicated operational mode for rapid and instinctive execution of a limited number of dedicated functions while being able to then switch into the icon operational mode for selecting and executing additional functions, such as, imaging functions, which may not be as frequently used as those functions associated with a dedicated pedal actuator. The system of the invention, while providing easy dedicated operation of certain functions is also readily expandable due to the icon mode and the icon display. LEDs on the system body provide quick visual indication as to the mode of the system.

In a preferred embodiment of the invention, the control system utilizes an audible indicator which is operable to sound when the visual indicator is moved through the various segments of the icon display. Furthermore, the control system has a memory which maintains the selected icon function in the icon operational mode even when the control system has been switched to the dedicated mode. For example, if an x-ray function has been selected in the icon operational mode, the system may be switched to the dedicated mode and the table top may be moved by one of the dedicated pedals without affecting the selection in the icon mode. Subsequently, the control system may be switched back to the icon operational mode once the table is properly positioned, and the x-ray function may be immediately executed without having to scroll back through the icon display with the various actuator pedals to again properly select the x-ray function. Therefore, the control system of the invention provides rapid cooperation between the two modes so that the control system may be set up with a selected function in the icon mode without being affected when it is subsequently utilized in the dedicated mode.

In a preferred embodiment, the body of the control system includes a protective bar extending around the front thereof which protects inadvertent actuation of a pedal by the operator.

In an alternative embodiment of the invention, the control system comprises actuator switches instead of pedals. In the center of the body, the dedicated forward, back, left and right functions of the table top are implemented by four switches in the center of the body to replace the cross-shaped joystick actuator of the previously described embodiment. In the alternative embodiment, the dedicated table top controls also select and actuate functions from the icon display instead of the dedicated elevation and tilt controls as with the previously-described embodiment. The right-most switch scrolls the visual indicator through the icon display in one direction while the left most switch scrolls the visual indicator in the opposite direction when the system is in the icon mode. The forward and back switches then execute the selected function when actuated in the icon mode. Two switches for moving the table top up and down in elevation are positioned at the rearwardmost edge of the body on one side of the body while two other actuator switches for rotating and tilting the table in opposite directions are positioned also at the rearwardmost edge on the other side of the body. In the alternative embodiment, the elevation and tilt switches are always dedicated to their particular functions regardless of the operational mode of the control system.

The inventive system is operable such that if two actuators are contemporaneously engaged, the system will execute only the function associated with the first-engaged actuator and will not actuate another function until all actuators are then disengaged and then an actuator is subsequently re-engaged. This prevents undesired continuous execution of a function when the function's actuation is disengaged but another actuator remains inadvertently engaged.

The preferred embodiment of the present invention is described with foot control actuators for a urology table which move the table top and also activate x-ray, tomography and fluoroscopy equipment. However, it will be appreciated that the control system of the present invention might be utilized for any number of multi-function apparatuses which might be more easily operated with a number of dedicated actuators and functions in conjunction with additional functions which are selectable from a function menu.

The above and other objectives and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
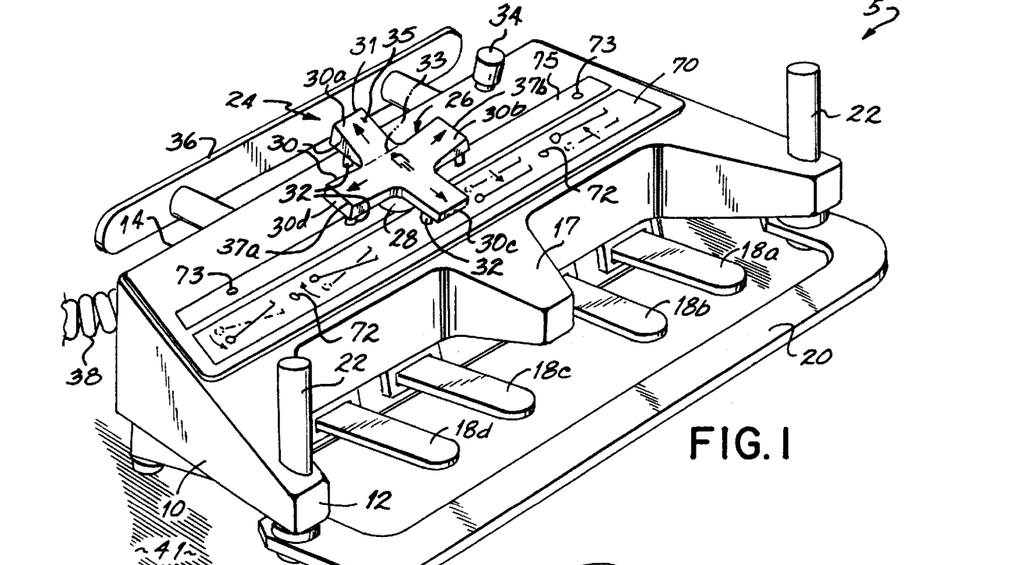
FIG. 1 is a perspective view of an embodiment of the foot-operated control system of the present invention.

Referring to FIG. 1, the foot-operated control system 5 of the present invention includes a body 10 which is generally sloped upwardly from a frontmost side 12 to a rearwardmost side 14 to coincide with the upward sloping of the foot of an operator (not shown) which will generally be pivoted at the heel. The operator's foot will generally be positioned such that the heel is proximate the frontmost side 12 and the toe or ball region of the foot is used to engage the system actuators. Body 10 includes two indentations on the left and right sides of the body for access to pedal actuators 18a, 18b, 18c and 18d for control of a multi-function apparatus (see FIG. 3) with the foot-operated control system 5. Safety bar 20 extends around the frontmost side 12 of body 10 and prevents inadvertent actuation of pedal actuators 18a–18d. Safety bar 20 also provides a sensual indication to the foot of the operator that the foot is proximate the control system 5. Positioning pins 22 on either side of body 10 confine the side-to-side motion of the foot to keep it contained over the actuator pedals 18a–18d. A projection section 17 of body 10 separates the right-side pedals 18a, 18b from the left-side pedals 18c, 18d and also provides sensual indication of the location of the various control system actuator pedals to an operator.

The control system 5 further comprises a joystick actuator 24 which includes a cross-shaped actuator pedal 26 which pivots on a shaft 28. The individual legs 30 of the cross-shaped pedal 26 provide four different pivot directions for the execution of four different functions as described further hereinbelow. The cross-shaped pedal 26 is preferably metal and beneath each leg 30 is provided a proximity switch 32 which detects the presence of the metal legs 30 when a particular leg is depressed downwardly toward the switch 32. Pedal 26 can thus be pivoted in four different directions for executing four dedicated functions. Body 10 further includes a mode switch 34 which is preferably a simple button switch which may be alternately opened and closed by depression from an operators foot. Mode switch 34 switches the control system 5 between the dedicated operational mode and the icon operational mode to provide an operator with selection and execution of the functions of a multi-function apparatus by either choosing an icon or by engaging a dedicated actuator as described further hereinbelow. A handle 36 on the body provides mobility for the control system which may be picked up and positioned at a desired location proximate the multi-function apparatus with which it is used. Line 38 couples the control system 5 with the multi-function apparatus (see FIG. 3).

In accordance with the principles of the present invention, the control system 5 may be selectively operated in either a dedicated operational mode or an icon operational mode. In the dedicated operational mode, each of the actuators is associated with a dedicated function of the multi-function apparatus; however, in the icon operational mode, at least one of the actuation devices, such as pedal 18a, is operable to make the control system 5 select one of a plurality of selectable functions from an icon display. Another one of the actuator pedals such as pedal 18c is operable to cause the system 5 to actuate the multi-function apparatus to execute the selected function. Accordingly, an operator may utilize the foot-operated control system 5 of the invention either in the icon mode or the dedicated mode for executing the selected functions of the multi-function apparatus. In the embodiment of the invention illustrated is FIG. 1, the cross-shaped actuator 24 is always dedicated to the table top motion regardless of the system mode, and thus will move the table top whether the system is in the icon or dedicated mode.

Figure 3:
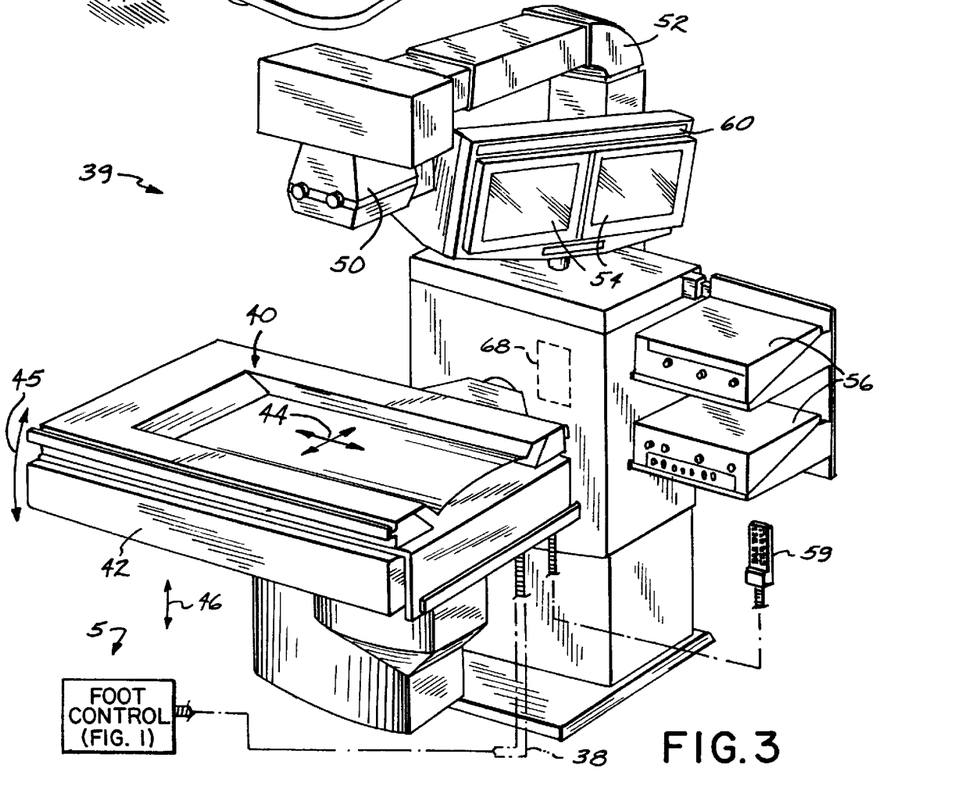
FIG. 3 is a perspective view of an automated urological table utilized with the foot-operated control system of the present invention.

In a preferred embodiment of the invention, the control system 5 is specifically adapted for use with a urology table having a movable table top to support a patient, as well as x-ray, tomography and fluoroscopy equipment for taking pictures of the patient on the table top. Referring to FIG. 3, one such urology table 39 is shown attached to control system 5 by line 38 and preferably is the Hydradjust IV Urological Table or HUT IV available from Liebel-Flarsheim Company of Cincinnati, Ohio. The table 39 comprises a movable table top 40 which is operable to slide left, right, forward and reverse on platform 42 as indicated by reference arrows 44. Furthermore, the entire table top 40 and support platform 42 are rotatable in opposing directions as indicated by reference arrows 45 to tilt the head or feet of a patient (not shown) on the table top 40. Table top 40 and platform 42 are also operable to be raised or lowered elevationally as indicated by reference arrow 46. Table 39 also includes x-ray, tomography and fluoroscopy equipment indicated collectively by camera 50 attached to a movable support arm 52. Monitors 54 provide real time viewing of images perceived by the camera equipment 50. The table may also include additional diagnostic electronics 56. A hand-held device 59 might also be available in addition to the foot-operated control system 5 for controlling the table and imaging functions. Additional information regarding operation of the HUT IV table is available from Liebel-Flarsheim.

Figures 2, 3A:
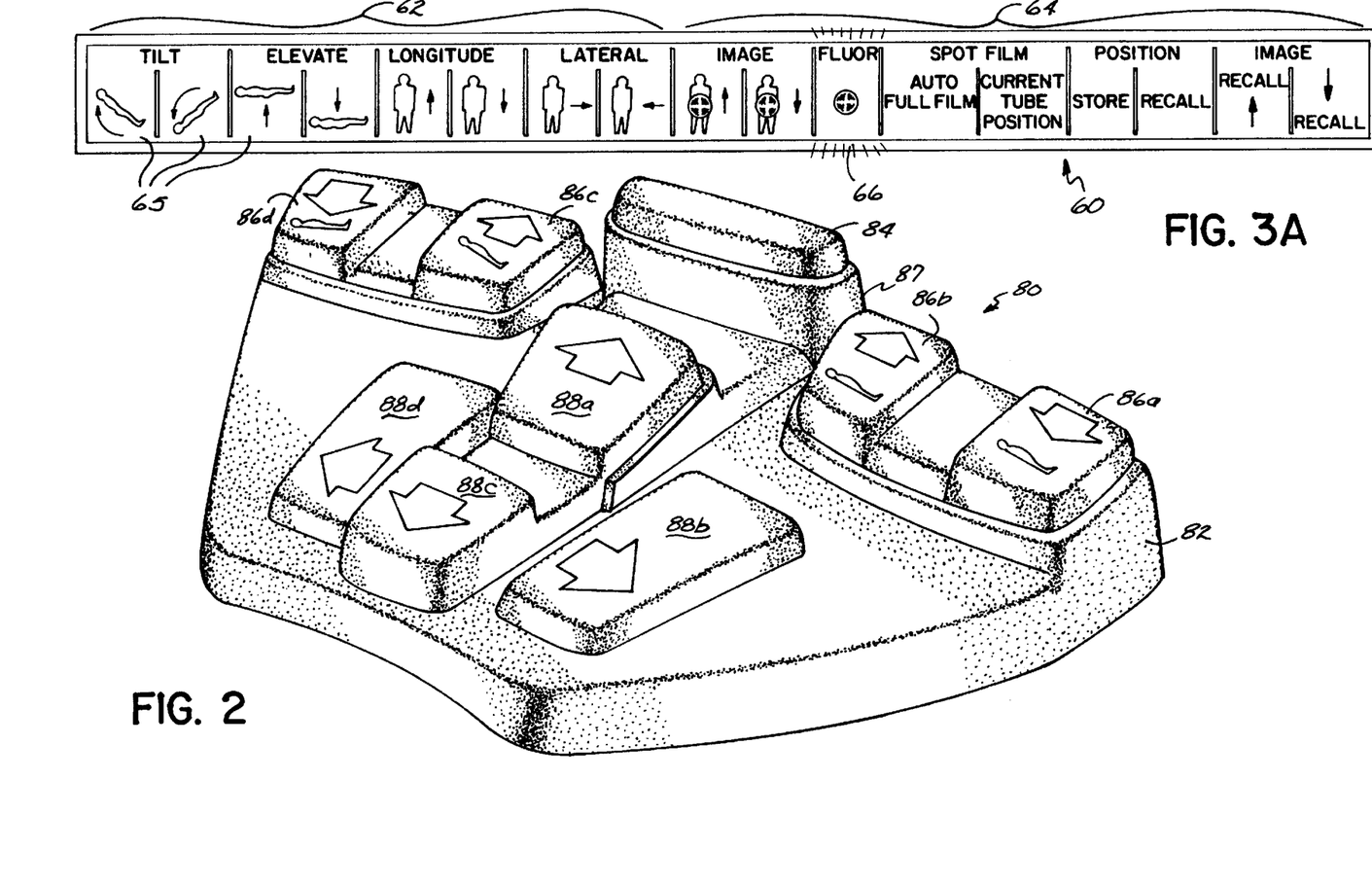
FIG. 2 is a perspective view of an alternative embodiment of the foot-operated control system of the present invention.
FIG. 3a is an embodiment of an icon display utilized with the foot-operated control system of the present invention and specifically used in conjunction with the urological table of FIG. 3.

On top of the monitors 54 is an icon display 60 which serves as a function menu for movement of the table and operation of the imaging functions. Referring now to FIG. 3a, one embodiment of icon display 60 is illustrated setting forth various table top and imaging functions available with the HUT IV table. It will be understood by a person of ordinary skill in the art that such icon display might include additional table functions as well as additional imaging functions to be selected or may include completely different functions depending upon the multi-function apparatus. Additionally, a video monitor might provide display of the selectable functions. Icon display 60 may generally be separated into a table top portion 62 and an imaging control portion 64. Icon display 60 is divided into individual icon segments 65 which preferably include graphics directed to the particular table movement or imaging function which is being selected. Through the use of the foot-operated control system 5, a visual indicator such as a backlight 66 is moved through the sequential segments 65 of the icon display 60. Referring again to FIG. 1, when the control system 5 is in the icon operational mode, engagement or depression of actuator pedal 18a with the operator's foot will move the visual indicator 66 through the icon display in one direction, preferably to the right side of the display 60. If pedal 18a is held down, the indicator 66 will continue to scroll right. A speaker of the systems provides an available indication that segments 65 are being selected. Engagement of pedal actuator 18b will move the visual indicator 66 through the display in the opposing direction, preferably to the left (see FIG. 3A). Constant depression of pedal 18b, scrolls left. That is, the right and left actuator pedals, 18a, 18b, respectively, correspond to right or left movement of the indicator 66. When the visual indicator is backlighting a desired icon segment 65 which corresponds to a desired function, the selecting pedal 18a or 18b is disengaged so the visual indicator 66 stops at the selected icon segment. Selection of the icon segment 66 actually selects the function corresponding to the segment for execution. Subsequent engagement of either of the pedal actuators 18c or 18d will produce an actuation signal from system 5 which is sent via line 38 to a controller of table 39. The actuation signal is preferably in the form of a command from a processor of the system 5 sent to a controller for the table as discussed further hereinbelow. Depending upon the selected function, table 39 will either execute a table top function or an imaging function. As may be appreciated, if a multi-function apparatus other than table 39 is utilized, some other function might be selected and executed. Table 39 includes an internal controller indicated in phantom by block 68 as well as various mechanical elements (not shown) for executing the selected function.

When control system 5 is in the dedicated operational mode, each pedal actuator 18a–18d and the various legs of the cross-shaped joystick actuator 24 are dedicated to specific functions. Engagement of any such actuator in the system will produce an execution of the dedicated function. For example, in the embodiment of the control system 5 illustrated in FIG. 1, pedal actuator 18a corresponds to raising the height of table top 40 and platform 42. Corresponding to the various pedal actuators is a graphics display 70 which graphically depicts movement of a body on a table when the particular actuator pedal is engaged. Similar to actuator pedal 18a, engagement of actuator pedal 18b lowers the elevation of the table top 40 while the actuators pedals 18c, 18d rotate and tilt the table top to tilt the body thereon as seen by the graphics on display 70. Corresponding sets LEDs 72, 73 are lit to indicate that the system is in the icon or dedicated mode. The LED set 72 when illuminated shows the operator that the system is dedicated, the LED set 73 shows that the icons may be selected. A graphics display 75 shows that pedals 18a, 18b are for scrolling left and right through the icon segments 65 and pedals 18c, 18d are for activating or executing the selected functions. As mentioned, the cross-shaped joystick actuator 24 is always utilized to executed dedicated movements of the table top 40 regardless of the mode of the control system 5. When an operator's foot depresses one of the legs 30 of pedal 26, the table top will slide in a direction corresponding to an arrow on the particular leg 30. With actuator 24, the table top 40 may be moved from side-to-side, forward and then back. In a preferred embodiment, the left and right arrows of the center legs 30b, 30d as illustrated in FIG. 1 show that those legs move the table top left or right and the up and down arrows illustrated on the rearwardmost and forwardmost legs 30a, 30c show that those legs will move the table top forward and then back. The rearwardmost leg and side legs are wedge shaped so that the engagement surface on those legs are elevated to prevent inadvertent depression of one leg when the operator desires to depress a leg. For example, the rearwardmost leg 30a is wedged shaped to have a rearwardmost edge 31 which is elevated higher than the edge 33 to present a raised, sloped surface 35 on leg 30a. When an operator's foot (not shown) is positioned to engage leg 30a and surface 35, the foot will be able to easily engage leg 30a without engaging the other legs which will have top surfaces generally below top surface 35. The operator can thus execute the dedicate function corresponding to the engaged leg without inadvertently engaging other legs 30 of actuator 24. Since the rearwardmost leg 30a is of farthest away with respect to an operator, the unique wedge-shaped construction of leg 30a provides easy access and engagement without requiring the operator to unnecessarily lift and maneuver his foot to engage leg 30a.

Similarly, the side legs 30b, 30d are also wedged shaped such that the legs are thickest at the outer most edges 37, 39, respectively to provide sloped, raised surfaces similar to surface 35. However, the slope angles of the wedge-shaped side legs 30b, 30d are less than the slope angle of leg 30a so that the top surfaces of legs 30b, 30d are lower than surface 35 of leg 30a. In that way, the operator may more easily engage one of the side legs 30b, 30d without inadvertently engaging the forwardmost leg 30c but will not generally engage leg 30b or 30d when attempting to engage leg 30a. The forwardmost leg 30c is closer to the operator's foot and therefore is preferably of uniform thickness throughout its length because it will be the easiest leg to engage. Therefore, the effective heights of the upper surfaces of the legs, such as surface 35, are increased above a floor surface 41 the further the particular leg is away from the safety bar 20 and the forwardmost side 12 of body 10. Again, this insures that the leg 30 selected by the operator is actually engaged without requiring excessive movement of the operator's foot. Further illustration of the cross-shaped actuator is provided in a design patent application entitled ACTUATOR FOOT-OPERATED CONTROL SYSTEM and filed on even date herewith.

FIG. 2 illustrates an alternative embodiment of the foot control system of the present invention. Referring to FIG. 2, control system 80 includes a body 82, to be positioned on a floor proximate a multi-function apparatus being controlled. A depressible, two-state mode switch 84 selectively changes operation of the control system from a dedicated operational mode to an icon operational mode as previously described. In the embodiment of FIG. 2, the actuator elements are arranged differently from the embodiment of FIG. 1 for different foot engagements. System 80 comprises a plurality of depressible switches which are coupled to pedal actuators. The pedal actuators are depressed to actuate the switches and generate actuation signals or selection signals. Specifically, actuator pedals 86a, 86b, 86c and 86d are arranged at rearwardmost side 87 of body 82, for controlling elevational and tilting movement of the table top 40. Each of the pedals, 86a–86d are dedicated regardless of the operational mode of system 80. When the pedals are depressed, they execute a dedicated function preferably shown by graphics on the pedal. For example, actuator pedal 86a, when depressed lowers table top 40, while actuator pedal 86b raises table top 40. Similarly, actuator pedal 86c tilts the table top in one direction, while actuator pedal 86d tilts the table top in another direction. Pedals 88a, 88b, 88c, and 88d move the table top horizontally when the system 80 is in dedicated operational mode according to the graphic arrows on the pedals. Particularly, depression of pedal 88a moves the table top in a forward direction, and actuator pedal 88c moves the table top in a rearward direction. Actuators pedals 88b and 88d move the table top to the right or to the left, respectively. When mode switch 84 is depressed, actuator pedal 88b scrolls the visual indicator through the icon display in one direction (preferably to the right), and actuator pedal 88d scrolls the indicator in the opposite direction (preferably to the left). When a function has been selected from the icon display, depression of either actuator pedal 88a or 88c, produces an actuation command for the multi-function apparatus to execute the selected function. As with the embodiment illustrated in FIG. 1, the system of FIG. 2 might be utilized with a multi-function apparatus other than a urological table, and dedicated functions or selected functions may relate to something other than table top movement or imaging equipment.

Figure 4:
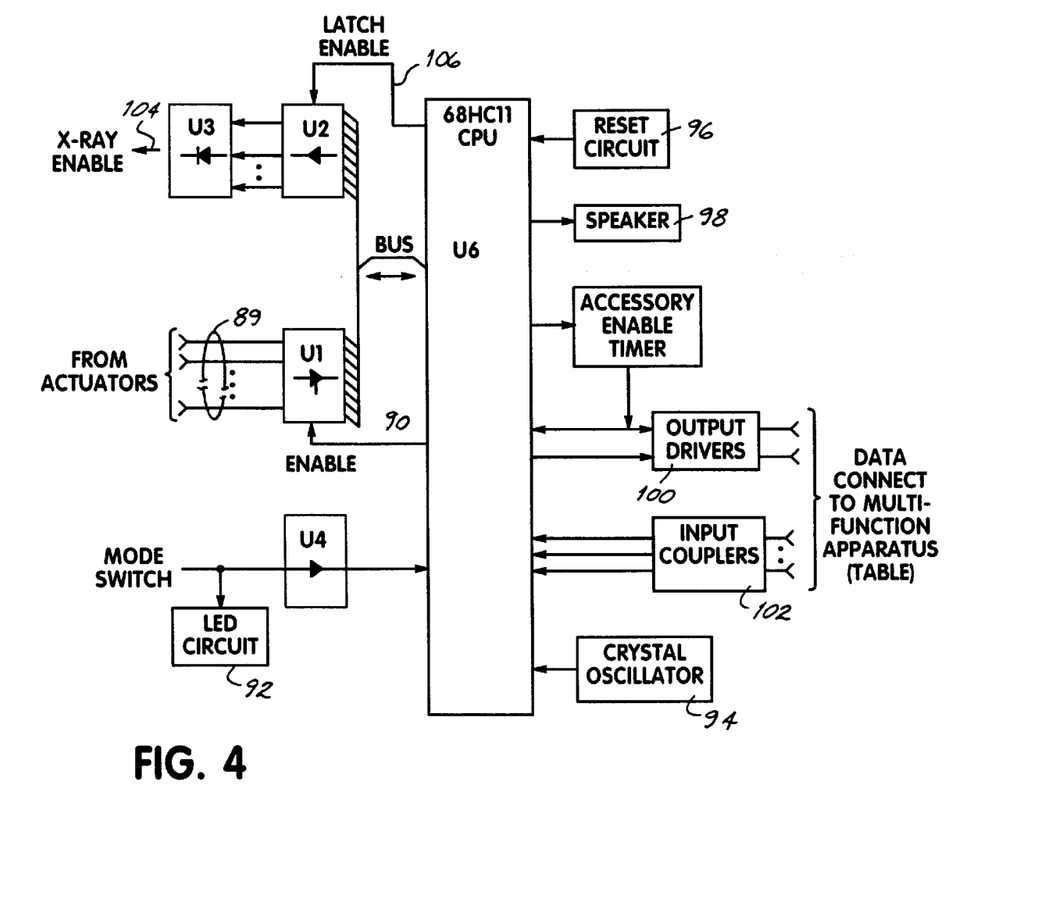
FIG. 4 is a block diagram of the processor and supporting circuitry utilized in the control system of the invention.

FIG. 4 is a block diagram of the control electronics of an embodiment of the foot-operated control system of the present invention. The system includes a processor U6 which is preferably an MC68HC811E2 available from Motorola. The various actuators of the foot-operated control system of the invention are coupled to processor U6 through an appropriate buffer circuit U1 which is enabled by processor U6 through line 90 to accept inputs from the various actuator pedals, switches or joysticks of the system. The buffers are enabled whenever processor U6 is receiving data or switching signals from the actuators. The input from the mode switch 34 as provided to processor U6 through a separate buffer U4. The output from the mode switch is also coupled to an LED circuit 92 which will light the appropriate LED sets 72, 73 on the control system body 10 as appropriate to indicate to an operator that the control system 5 is in the dedicated mode or the icon mode.

Processor U6 is appropriately supported by a crystal oscillator circuit 94 and reset circuit 96 which initializes the processor upon initial power-up. Processor U6 also controls a speaker 98 which appropriately sounds when the system is in the icon operational mode and the visual indicator 66 is moving through the various segments 65 of icon display 60 as described above. When a particular actuator is engaged as indicate by inputs from buffer U1, the processor U6 creates a message which is sent to the multi-function apparatus, such as a urological table, over a data connection carried by line 38. The individual input and output lines of the data connection are appropriately interfaced with processor U6 through output drivers 100 and input couplers 102. The data connection interfaces with the control circuitry of the multi-function apparatus, such as controller 68 of table 39 (see FIG. 3).

Processor U6 also provides an x-ray enable output signal on line 104 for enabling any x-ray, tomography and/or fluoroscopy functions of table 39. Whenever the mode switch indicates that control system 5 is in an icon operational mode and an actuator has been engaged to generate an actuation signal in one of the appropriate actuator input lines 89, the imaging equipment is enabled by the signal on line 104. If an imaging function is selected, that function will be executed. Processor U6 provides the output signal on line 104 through a series of buffers U2 and U3. Buffer U2 is enabled by latch enable line 106 to produce the x-ray enable signal on line 104. As may be appreciated by a person of ordinary skill in the art, numerous other output lines might be provided through buffers U2 and U3 for enabling other functions. The x-ray enable line 104 prevents inadvertent actuation of the imaging system of table 39 when the foot-operated control system 5 is in a dedicated mode for moving the table top. In a preferred embodiment of system 5 illustrated in FIG. 1, all the dedicated functions are directed to movement of the table top 40 and the platform 42 and none are dedicated to imaging. Therefore, the x-ray enable line 104 prevents any inadvertent actuation of x-ray equipment when the system is in a dedicated mode.

Figures 5, 6, 7:
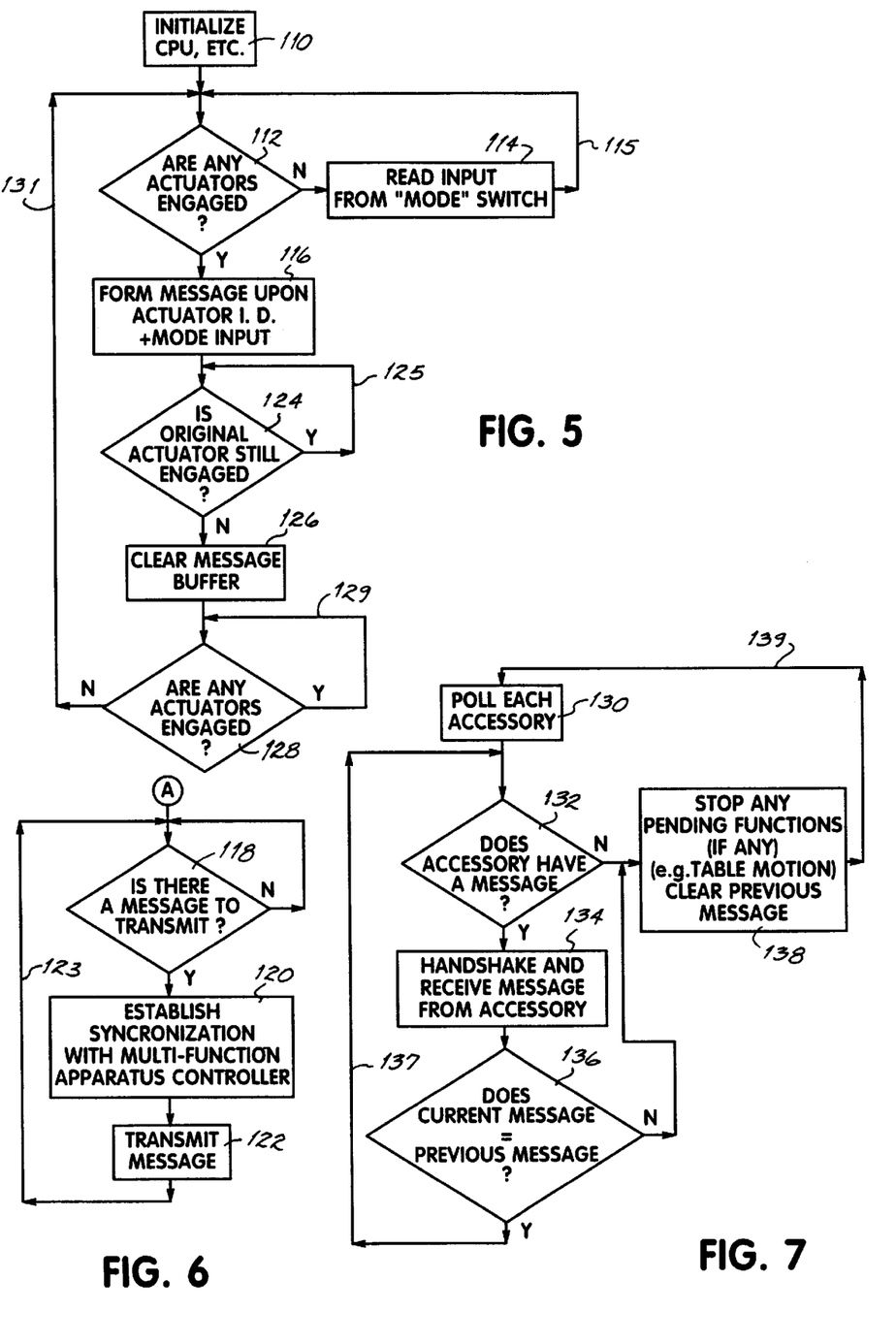
FIGS. 5, 6 and 7 are operational flow charts illustrating the operation of the foot-operated control system of the invention as utilized with a urology table.

FIGS. 5, 6 and 7 illustrate software flow charts for operation of the inventive control system. Referring to FIG. 5, when the system is initially powered, the CPU or processor U6 is initialized and other mechanical or electrical structures are provided with power as appropriate depending upon the multi-function apparatus which is controlled by system 5 (box 110). After power-up, the processor U6 determines whether any actuators are engaged (box 112). If none of the actuators are engaged, the processor U6 reads the input from the mode switch 34 (box 114) and returns in a loop 115 to check if any actuators are now engaged. The system will continue to check the actuators to see if they are engaged. Upon sensing that an actuator is engaged, the processor U6 forms a message depending upon which actuator is actually engaged and also the state of the mode switch input (box 116). For example, the message might be a "table-up" message if actuator pedal 18a is depressed and the system 5 is in the dedicated operational mode. Alternatively, if pedal 18a is depressed with the system in the icon operational mode, the message will be a command to "scroll right" in the icon display 60. The message will then be ready for transmission to the multi-function apparatus.

Contemporaneously, with the polling of the actuators by processor U6, another operational program continuously checks see if there is a message. Referring to FIG. 6, if there is no message to transmit, the processor will continue to check as illustrated by box 118. If there is a message, the processor U6 establishes synchronization with the control device of the multi-function apparatus, such as controller 68 of table 39 (box 120). Once synchronization has been established, the message is transmitted to the controller 68 for execution of a particular function, such as tabletop movement or imaging (box 122). As illustrated by FIG. 6 and loop 123, the message transmission sequence will continue to run to ensure that all messages are transmitted.

Returning now to FIG. 5, the processor determines if the original actuator which initiated the last message is still engaged (box 124). If it is, the message will continue to be transmitted according to the flow chart of FIG. 6. As a result, the selected function will continue to be executed as long as the actuator is engaged. As illustrated by the loop 125, the processor will continue to monitor the originally engaged actuator to determine if it is still engaged. Upon sensing that it is no longer engaged, the message buffer will be cleared (box 126). Upon clearing the message buffer to stop execution of the function, the processor will again determine whether any actuators are engaged (box 128). If any are engaged, which means that they were contemporaneously engaged with the original actuator, the system will go into a stall mode as indicated by loop 129 until all actuators are disengaged. When all actuators are finally disengaged, the processor U6 will operationally return to block 112 via loop 131 and begin to again determine which actuators are engaged and then send an appropriate message. In that way, the control system 5 of the present invention prevents continuous actuation of a function when a particular actuator has been disengaged but another actuator was engaged contemporaneously with the first actuator. For example, if the actuator pedal 18a is engaged to raise the level of the tabletop 40, and then the actuator pedal 18d is contemporaneously engaged to tilt the table, when the operator's foot is removed from pedal actuator 18a, the control system will operate in a hold mode and will not begin tilting the table or will not continue to raise the table until all actuators are disengaged and subsequently an actuator for a desired function is reengaged. This control system 5 thus prevents continuation of the original function, i.e., raising of the bed, when a different actuator pedal is engaged. As such, only one function may be actuated at a time regardless of how many other actuators are contemporaneously engaged. If several actuators are engaged, The control system will wait until all actuators are disengaged and then subsequently the desired actuator is reengaged.

FIG. 7 is a flow chart for the interaction between the control system of the invention and a multi-function apparatus. In one embodiment of the invention discussed herein, the apparatus is a urological table which is connected to the control system 5 and to a hand controller 58. During operation, the multi-function apparatus checks each control accessory to determine if there is any communication (block 130). The apparatus checks each accessory for a message (block 132). If there is a message, a handshake routine is initiated for the multi-function apparatus to receive the message, such as a message from the foot-operated control system 5 (block 134). As long as the current message being received is the same message as the previous message received by the multi-function apparatus, the system will continue to request the message from the accessory, i.e., control system 5, as indicated by block 136 and loop 137. However, if the current message is a different message, the multi-function apparatus stops any pending functions, such as table motions, and clears the message (block 138) as indicated by loop 139. The apparatus then returns to poll each control accessory for subsequent messages. In that way, each function of the apparatus is isolated and will cease before another function is subsequently executed.

The control system 5 foot-operated control system 5 of the present invention is able to operate and control a multi-function apparatus, such as a urological table, which has a variety of different executable functions. Functions may be selected according to dedicated actuators or may be chosen from selectable functions along an icon display. While a preferred embodiment of the invention is designed for a urological table, the actuators and selectable functions of the icon display could just as easily be incorporated to control another multi-functional device with other selectable and executable functions.

The foot-operated control system of the present invention of the present invention is relatively small and mobile and may be easily manipulated around the apparatus with which it is utilized. The dedicated operational mode of the system provides an operator with dedicated actuators so that instinctive, sensual operation may be established for frequently used functions of the apparatus. While such dedicated operation is achievable with the invention, other functions might also be controlled and added to the system without increasing its complexity and size and without spacing the actuators too closely or making them too small which would make engagement difficult. The icon mode of the invention provides for selection of functions along an icon display without requiring a specific dedicated actuator.

Actuators already existing in the system may be utilized for function selection and also for actuation of the selected function.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A foot-operated control system to be coupled to a multi-function apparatus to actuate at least one function of the multi-function apparatus, the control system comprising:

a body for positioning on a floor surface;

a mode switch on the body manipulatable by the foot of an operator, the mode switch operable for switching the control system between a dedicated non-display related operational mode wherein dedicated functions may be actuated directly by engaging a dedicated actuator in the multi-function apparatus and an icon operational mode wherein selectable functions comprising at least one of said dedicated functions and additional functions may be first selected by choosing a displayed icon and then actuated in the multi-function apparatus when the control system is coupled to the multi-function apparatus;

a first actuator supported by the body to be engaged by the operator's foot, the control system operable for being able to activate a first non-selected and dedicated function of the multi-function apparatus when said first actuator is engaged with the control system in the dedicated operational mode;

a second actuator supported by the body to be engaged by the operator's foot, the control system operable for being able to activate a second non-selected and dedicated function of the multi-function apparatus when said second actuator is engaged with the control system in the dedicated operational mode;

said first actuator further operable such that the control system generates a selection signal when the first actuator is engaged with the control system in the icon operational mode, the selection signal being for providing selection of one of a plurality of selectable functions of the multi-function apparatus;

said second actuator further operable such that the control system generates an actuation signal when the second actuator is engaged with the control system in the icon operational mode, the actuation signal being for providing actuation of said selected function of the multi-function apparatus;

whereby the multi-function apparatus may be selectively operated by a single system in both the dedicated operational mode to actuate dedicated functions of the apparatus and also in the icon operational mode for selecting and actuating selectable functions of the apparatus at the discretion of the operator.

2. The foot-operated control system of claim 1 further comprising a third actuator wherein the control system is operable for actuating a dedicated function of the multi-function apparatus when said third actuator is engaged with the control system in the dedicated operational mode, said third actuator operable for generating a selection signal when engaged with the control system in the icon operational mode, the control system responsive to said selection signal for selecting a function of the multi-function apparatus.

3. The foot-operated control system of claim 1 further comprising a fourth actuator wherein the control system is operable for actuating a dedicated function of the multi-function apparatus when said fourth actuator is engaged with the control system in the dedicated operational mode, said fourth actuator operable for generating an actuation signal when engaged with the control system in the icon operational mode, the control system responsive to said actuation signal for actuating the selected function of the multi-function apparatus.

4. The foot-operated control system of claim 1 further comprising an icon display and a visual indicator operably coupled to the actuators, the icon display including a plurality of visually selectable segments which correspond to selectable functions of the multi-function apparatus, the visual indicator moving through the segments of the icon display in response to engagement of the first actuator in the icon operational mode and indicating the selected segment when the first actuator is subsequently disengaged.

5. The foot-operated control system of claim 4 wherein the control system is further operable for actuating the function corresponding to the selected segment when the second actuator is engaged in the icon operational mode.

6. The foot-operated control system of claim 4 further being operable to maintain the selected segment and function in the icon mode when the mode switch is engaged to place the system in the dedicated operational mode, another function being actuatable in the dedicated mode and the visual indicator returning to said selected segment when the system is subsequently returned to said icon mode.

7. The foot-operated control system of claim 4 further comprising an audible indicator which is operable to sound when said visual indicator is moved from one segment to the next sequential segment.

8. The foot-operated control system of claim 1 further comprising a guard member coupled to the body proximate at least one actuator to prevent inadvertent engagement of the actuator by the operator's foot.

9. The foot-operated control system of claim 1 further comprising a dedicated actuator wherein the control system is operable for activating a dedicated function when the dedicated actuator is engaged regardless of whether the system is in the icon or dedicated mode.

10. The foot-operated control system of claim 9 wherein said dedicated actuator comprises a cross-shaped member with a plurality of legs.

11. The foot-operated control system of claim 10 wherein at least one of said legs of said cross-shaped member has an engageable surface which is elevated higher than an engageable surface of another of said legs for easier engagement of at least one leg by the foot of the operator without inadvertent engagement of said other leg.

12. An apparatus for performing a plurality of different functions comprising;

a mechanical structure operable to execute a plurality of functions, the mechanical structure including a controller for controlling execution of one of said functions in response to an actuation signal;

a foot-operated control system coupled to said mechanical structure controller for selecting at least one function from said plurality of functions and for providing an actuation signal for execution of the selected function, the control system comprising:

a body for positioning on a floor surface;

a mode switch on the body manipulatable by the foot of an operator, the mode switch operable for switching the control system between a dedicated non-display related operational mode wherein dedicated functions are actuated directly by engaging a dedicated actuator in the mechanical structure and an icon operational mode wherein selectable functions comprising at least one of said dedicated functions and additional functions are first selected by choosing a displayed icon and then actuated in the mechanical structure;

a first actuator supported by the body and engageable by an operator's foot, the control system operable for generating an actuation signal for execution of a non-selected function dedicated to the first actuator when said first actuator is engaged with the control system in the dedicated operational mode;

a second actuator supported by the body and engageable by the operator's foot, the control system operable for generating an actuation signal for execution of a different non-selected function dedicated to the second actuator when said second actuator is engaged with the control system in the dedicated operational mode;

said first actuator further operable such that the control system generates a selection signal when the first actuator is engaged with the control system in the icon operational mode, the selection signal providing selection of one of a plurality of selectable functions from the plurality of functions of the mechanical structure;

said second actuator further operable such that the control device generates an actuation signal when the second actuator is engaged with the control device in the icon operational mode, the actuation signal providing execution of the selected function by the mechanical structure through said controller;

whereby the single apparatus may be selectively operated in both the dedicated operational mode to actuate dedicated functions of the mechanical structure and also in the icon operational mode for selecting and actuating selectable functions of the mechanical structure at the discretion of the operator.

13. The apparatus of claim 12 wherein the control system further comprises an icon display and a visual indicator operably coupled to the actuators, the icon display including a plurality of visually selectable segments which correspond to selectable functions of the mechanical structure, the visual indicator moving through the segments of the icon display in response to engagement of the first actuator in the icon operational mode and indicating the selected segment and function when the first actuator is subsequently disengaged.

14. The apparatus of claim 13 wherein the control system is further operable to generate an execution signal for the function corresponding to the selected segment when the second actuator is engaged in the icon operational mode.

15. The apparatus of claim 13 wherein the system is further operable to maintain the selected segment and function in the icon mode when the mode switch is engaged to place the system in the dedicated operational mode, another function being actuatable in the dedicated mode and the visual indicator returning to said maintained selected segment when the system is subsequently returned to said icon mode.

16. The apparatus of claim 13 wherein the control system further comprises an audible indicator which is operable to sound when said visual indicator is moved from one segment to the next sequential segment.

17. The apparatus of claim 12 wherein the mechanical structure comprises a movable table top, the plurality of functions including directional movement of the table top.

18. The apparatus of claim 17 wherein the mechanical structure comprises at least one radiation device for photographing a person on the table top, the plurality of functions including different operational modes of the radiation device.

19. The apparatus of claim 18 wherein the control system further comprises an icon display and a visual indicator operably coupled to the control device, the icon display including a plurality of visually selectable segments which correspond to one of table top directional movement and radiation device operational modes, the visual indicator moving through the segments of the icon display in response to engagement of the first actuator in the icon operational mode and indicating the selected segment and function when the first actuator is subsequently disengaged.

20. The apparatus of claim 19 wherein the control system is further operable to maintain a selected radiation device operational mode segment and function in the icon operational mode when the mode switch is engaged to place the device in the dedicated operational mode, a table top directional movement function being actuatable in the dedicated operational mode and the visual indicator returning to said maintained operational mode segment when the device is subsequently returned to said icon operational mode.

* * * * *

UNITED STATES PATENT AND TRADEMARK OFFICE
CERTIFICATE OF CORRECTION

PATENT NO. : 5,883,615

DATED : March 16, 1999

INVENTOR(S) : Frank M. Fago et al.

It is certified that error appears in the above-identified patent and that said Letters Patent is hereby corrected as shown below:

Cover page, title reads "FOOT-OPERATED CONTROL SYSTEM FOR A MULTI-FUNCTION" and should read --FOOT-OPERATED CONTROL SYSTEM FOR A MULTI-FUNCTION APPARATUS--.

Column 2, line 38 reads "a large of different" and should read --a large number of different".

Column 9, line 18 reads "the dedicate function" and should read the --dedicated function--.

Column 9, line 26 reads "37.39." and should read --37a, 37b,-- as amended 11/30/98.

Column 10, line 9 reads "Actuators pedals" and should read --Actuator pedals--.

Column 10, line 47 reads "as indicate by" and should read --as indicated by--.

Column 12, line 17 reads "engaged, The" and should read --engaged, the--.

Column 12, lines 54 and 55 read "of the present invention of the present invention" and should read --of the present invention--.

UNITED STATES PATENT AND TRADEMARK OFFICE
CERTIFICATE OF CORRECTION

PATENT NO. : 5,883,615

DATED : March 16, 1999

INVENTOR(S) : Frank M. Fago et al.

It is certified that error appears in the above-identified patent and that said Letters Patent is hereby corrected as shown below:

Claim 1, lines 14, 15, and 16 read "apparatus when the control system is coupled to the multi-function apparatus;" and should read "apparatus;" as amended via 7/1/98 amendment.

Claim 1, line 19 reads "able to activate" and should read --able to actuate-- as amended via 7/1/98 amendment.

Claim 9, line 3 reads "for activating" and should read --for actuating-- as amended via 7/1/98 amendment.

Signed and Sealed this

Twenty-fifth Day of April, 2000

Attest:

Q. TODD DICKINSON

*Attesting Officer*     *Director of Patents and Trademarks*